(12) United States Patent
Rosenberg et al.

(10) Patent No.: US 10,293,140 B2
(45) Date of Patent: May 21, 2019

(54) ANCHOR DEVICE AND METHOD

(71) Applicant: INTERRAD Medical, Inc., Plymouth, MN (US)

(72) Inventors: Michael S. Rosenberg, Eagan, MN (US); Timothy J. Claude, Coon Rapids, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 130 days.

(21) Appl. No.: 15/171,540

(22) Filed: Jun. 2, 2016

(65) Prior Publication Data

US 2016/0279389 A1    Sep. 29, 2016

Related U.S. Application Data

(60) Continuation of application No. 14/293,125, filed on Jun. 2, 2014, now Pat. No. 9,381,323, which is a continuation of application No. 13/211,625, filed on Aug. 17, 2011, now Pat. No. 8,771,232, which is a continuation of application No. 12/553,555, filed on Sep. 3, 2009, now Pat. No. 8,016,813, which is a division of application No. 11/372,283, filed on Mar. 9, 2006, now Pat. No. 8,016,794.

(51) Int. Cl.
*A61M 25/02* (2006.01)
*A61M 25/04* (2006.01)
*A61B 17/34* (2006.01)

(52) U.S. Cl.
CPC ............ *A61M 25/02* (2013.01); *A61M 25/04* (2013.01); *A61B 2017/3484* (2013.01); *A61M 2025/0286* (2013.01)

(58) Field of Classification Search
CPC ... A61B 2017/3484; A61B 2017/3488; A61M 2025/0286; A61M 25/04
See application file for complete search history.

(56) References Cited

U.S. PATENT DOCUMENTS 1,242,314 A    10/1917  Bean
1,380,447 A     6/1921  Wescott
(Continued)

FOREIGN PATENT DOCUMENTS

EP        0341039        11/1989
WO    WO1991015254       10/1991
(Continued)

OTHER PUBLICATIONS

European Search Report in European Application No. 07758123.9, dated Jun. 20, 2017, 7 pages.
(Continued)

*Primary Examiner* — Deanna K Hall
(74) *Attorney, Agent, or Firm* — Fish & Richardson P.C.

(57) ABSTRACT

Some embodiments of an anchor device may include bendable anchor mechanism that is deployable in a subcutaneous layer to releasably secure the anchor device to a patient's body. Certain embodiments of the anchor mechanism may include one or more barbs that flexibly bend in response to an insertion or removal force. As such, the anchor mechanism may be inserted into a subcutaneous layer, and removed from the subcutaneous layer, without the need for a separate actuation device to extend or retract the barbs.

16 Claims, 10 Drawing Sheets

(56) References Cited

U.S. PATENT DOCUMENTS

| | | |
|---|---|---|
| 1,624,716 A | 4/1927 | Ferdinando |
| 1,998,225 A | 4/1935 | Frances |
| 2,525,398 A | 10/1950 | Collins |
| 3,039,468 A | 6/1962 | Price |
| 3,059,645 A | 10/1962 | Hasbrouck et al. |
| 3,108,595 A | 10/1963 | Overment |
| 3,176,690 A | 4/1965 | HDoubler |
| 3,308,819 A | 3/1967 | Arp |
| 3,630,195 A | 12/1971 | Santomieri |
| 3,677,250 A | 7/1972 | Thomas |
| 3,717,151 A | 2/1973 | Collett |
| 3,765,032 A | 10/1973 | Palma |
| 3,777,761 A | 12/1973 | Sheridan |
| 3,825,010 A | 7/1974 | McDonald |
| 3,834,380 A | 9/1974 | Boyd |
| 3,856,009 A | 12/1974 | Winnie |
| 3,896,527 A | 7/1975 | Miller et al. |
| 3,902,501 A | 9/1975 | Citron et al. |
| 3,938,529 A | 2/1976 | Gibbons |
| 4,043,346 A | 8/1977 | Mobley et al. |
| 4,083,370 A | 4/1978 | Taylor |
| 4,114,618 A | 9/1978 | Vargas |
| 4,164,943 A | 8/1979 | Hill et al. |
| 4,230,110 A | 10/1980 | Beroff |
| 4,248,224 A | 2/1981 | Jones |
| 4,278,092 A | 7/1981 | Borsanyi et al. |
| 4,309,994 A | 1/1982 | Grunwald |
| 4,397,647 A | 8/1983 | Gordon |
| 4,474,569 A | 10/1984 | Newkirk |
| 4,569,344 A | 2/1986 | Palmer |
| 4,592,356 A | 6/1986 | Gutierrez |
| 4,645,492 A | 2/1987 | Weeks |
| 4,665,906 A | 5/1987 | Jervis |
| 4,799,495 A | 1/1989 | Hawkins et al. |
| 4,804,359 A | 2/1989 | Grunwald et al. |
| 4,813,930 A | 3/1989 | Elliott |
| 4,936,823 A | 6/1990 | Colvin et al. |
| 4,986,279 A | 1/1991 | O'Neill |
| 4,986,810 A | 1/1991 | Semrad |
| 5,041,085 A | 8/1991 | Osborne et al. |
| 5,067,957 A | 11/1991 | Jervis |
| 5,088,979 A | 2/1992 | Filipi et al. |
| 5,122,122 A | 6/1992 | Allgood |
| 5,190,546 A | 3/1993 | Jervis |
| 5,253,643 A | 10/1993 | Price |
| 5,256,146 A | 10/1993 | Ensminger et al. |
| 5,257,975 A | 11/1993 | Foshee |
| 5,267,960 A | 12/1993 | Hayman et al. |
| 5,279,564 A | 1/1994 | Taylor |
| 5,312,337 A | 5/1994 | Flaherty et al. |
| 5,344,439 A | 9/1994 | Otten |
| 5,353,787 A | 10/1994 | Price |
| 5,354,279 A | 10/1994 | Hofling |
| 5,368,017 A | 11/1994 | Sorenson et al. |
| 5,377,667 A | 1/1995 | Patton et al. |
| 5,378,239 A | 1/1995 | Termin et al. |
| 5,391,156 A | 2/1995 | Hildwein et al. |
| 5,419,777 A | 5/1995 | Hofling |
| 5,456,671 A | 10/1995 | Bierman |
| 5,470,321 A | 11/1995 | Forster et al. |
| 5,496,277 A | 3/1996 | Termin et al. |
| 5,531,676 A | 7/1996 | Edwards et al. |
| 5,540,648 A | 7/1996 | Yoon |
| 5,578,013 A | 11/1996 | Bierman |
| 5,597,378 A | 1/1997 | Jervis |
| 5,599,311 A | 2/1997 | Raulerson |
| 5,616,131 A | 4/1997 | Sauer et al. |
| 5,653,718 A | 8/1997 | Yoon |
| 5,681,288 A | 10/1997 | Schlitt |
| 5,688,247 A | 11/1997 | Haindl et al. |
| 5,702,371 A | 12/1997 | Bierman |
| 5,707,362 A | 1/1998 | Yoon |
| 5,722,959 A | 3/1998 | Bierman |
| 5,728,133 A | 3/1998 | Kontos |
| 5,741,234 A | 4/1998 | Aboul-Hosn |
| 5,746,720 A | 5/1998 | Stouder, Jr. |
| 5,755,697 A | 5/1998 | Jones et al. |
| 5,769,821 A | 6/1998 | Abrahamson et al. |
| 5,792,115 A | 8/1998 | Horn |
| 5,800,402 A | 9/1998 | Bierman |
| 5,810,781 A | 9/1998 | Bierman |
| 5,814,065 A | 9/1998 | Diaz |
| 5,817,062 A | 10/1998 | Flom et al. |
| 5,827,230 A | 10/1998 | Bierman |
| 5,833,664 A | 11/1998 | Seare |
| 5,833,667 A | 11/1998 | Bierman |
| 5,857,999 A | 1/1999 | Quick et al. |
| 5,879,333 A | 3/1999 | Smith |
| 5,921,965 A | 7/1999 | Blei |
| 5,928,266 A | 7/1999 | Kontos |
| 5,944,732 A | 8/1999 | Raulerson et al. |
| 5,947,931 A | 9/1999 | Bierman |
| 5,971,960 A | 10/1999 | Flom et al. |
| 5,984,896 A | 11/1999 | Boyd |
| 5,989,265 A | 11/1999 | Bouquet De La Joliniere et al. |
| 6,090,072 A | 7/2000 | Kratoska et al. |
| 6,213,979 B1 | 4/2001 | Bierman |
| 6,217,527 B1 | 4/2001 | Selmon et al. |
| 6,217,554 B1 | 4/2001 | Green |
| 6,231,548 B1 | 5/2001 | Bassett |
| 6,290,676 B1 | 9/2001 | Bierman |
| 6,413,240 B1 | 7/2002 | Bierman et al. |
| 6,447,485 B2 | 9/2002 | Bierman |
| 6,533,762 B2 | 3/2003 | Kanner et al. |
| 6,540,693 B2 | 4/2003 | Burbank et al. |
| 6,572,588 B1 | 6/2003 | Bierman et al. |
| 6,582,388 B1 | 6/2003 | Coleman et al. |
| 6,582,403 B1 | 6/2003 | Bierman et al. |
| 6,638,234 B2 | 10/2003 | Burbank et al. |
| 6,663,600 B2 | 12/2003 | Bierman et al. |
| 6,679,851 B2 | 1/2004 | Burbank et al. |
| 6,695,861 B1 | 2/2004 | Rosenberg et al. |
| 6,770,055 B2 | 8/2004 | Bierman et al. |
| 6,786,892 B2 | 9/2004 | Bierman |
| 6,827,705 B2 | 12/2004 | Bierman |
| 6,837,875 B1 | 1/2005 | Bierman et al. |
| 6,896,665 B2 | 5/2005 | Picha et al. |
| 6,929,625 B2 | 8/2005 | Bierman |
| 6,958,044 B2 | 10/2005 | Burbank et al. |
| 6,972,003 B2 | 12/2005 | Bierman et al. |
| 7,018,362 B2 | 3/2006 | Bierman et al. |
| 7,056,286 B2 | 6/2006 | Ravenscroft et al. |
| 7,087,069 B2 | 8/2006 | Petrovic et al. |
| 7,247,150 B2 | 7/2007 | Bierman |
| 7,273,468 B2 | 9/2007 | Bedell |
| 7,377,910 B2 | 5/2008 | Katoh et al. |
| 7,753,889 B2 | 7/2010 | Rosenberg |
| 7,811,251 B2 | 10/2010 | Wenchell et al. |
| 7,931,658 B2 | 4/2011 | Rosenberg et al. |
| 7,935,127 B2 | 5/2011 | Rosenberg et al. |
| 8,016,794 B2 | 9/2011 | Rosenberg et al. |
| 8,016,813 B2 | 9/2011 | Rosenberg et al. |
| 8,038,653 B2 | 10/2011 | Rosenberg et al. |
| 8,142,401 B2 | 3/2012 | Rosenberg |
| 8,147,459 B2 | 3/2012 | Rosenberg |
| 8,235,948 B2 | 8/2012 | Rosenberg et al. |
| 8,252,004 B2 | 8/2012 | Rosenberg et al. |
| 8,328,764 B2 | 12/2012 | Rosenberg et al. |
| 8,444,603 B2 | 5/2013 | Rosenberg et al. |
| 8,579,864 B2 | 11/2013 | Rosenberg et al. |
| 8,585,654 B2 | 11/2013 | Rosenberg |
| 8,628,511 B2 | 1/2014 | Rosenberg |
| 8,715,295 B2 | 5/2014 | Rosenberg |
| 8,771,232 B2 | 7/2014 | Rosenberg et al. |
| 8,920,380 B2 | 12/2014 | Rosenberg |
| 8,974,434 B2 | 3/2015 | Rosenberg et al. |
| 8,986,257 B2 | 3/2015 | Rosenberg et al. |
| 9,056,187 B2 | 6/2015 | Rosenberg et al. |
| 9,227,040 B2 | 1/2016 | Rosenberg et al. |
| 9,283,355 B2 | 3/2016 | Rosenberg |
| 9,381,323 B2 | 7/2016 | Rosenberg |
| 9,545,503 B2 | 1/2017 | Rosenberg |
| 9,656,045 B2 | 5/2017 | Rosenberg et al. |
| 2001/0056261 A1 | 12/2001 | Lerman et al. |

(56) References Cited

U.S. PATENT DOCUMENTS

| | | |
|---|---|---|
| 2002/0068898 A1 | 6/2002 | McGuckin, Jr. et al. |
| 2002/0068899 A1 | 6/2002 | McGuckin, Jr. et al. |
| 2002/0120250 A1 | 8/2002 | Altman |
| 2002/0165489 A1 | 11/2002 | McGuckin, Jr. et al. |
| 2003/0040712 A1 | 2/2003 | Ray et al. |
| 2004/0176726 A1 | 9/2004 | Katoh et al. |
| 2005/0043685 A1 | 2/2005 | Schinkel-Fleitmann |
| 2005/0137498 A1 | 6/2005 | Sakal et al. |
| 2005/0187578 A1 | 8/2005 | Rosenbert et al. |
| 2005/0256458 A1* | 11/2005 | Howard ............ A61M 25/0043 604/174 |
| 2005/0256459 A1 | 11/2005 | Howard et al. |
| 2005/0273058 A1 | 12/2005 | Bierman |
| 2006/0079845 A1 | 4/2006 | Howard et al. |
| 2007/0021685 A1 | 1/2007 | Oepen et al. |
| 2007/0078397 A1 | 4/2007 | Westsrate |
| 2007/0106330 A1 | 5/2007 | Rosenberg |
| 2007/0225651 A1 | 9/2007 | Rosenberg et al. |
| 2007/0232997 A1 | 10/2007 | Glenn |
| 2008/0312599 A1 | 12/2008 | Rosenberg |
| 2009/0054843 A1 | 2/2009 | Lundqvist |
| 2009/0099527 A1 | 4/2009 | Rosenberg et al. |
| 2009/0326470 A1 | 12/2009 | Rosenberg |
| 2009/0326473 A1 | 12/2009 | Rosenberg et al. |
| 2010/0016801 A1 | 1/2010 | Rosenberg et al. |
| 2010/0241084 A1 | 9/2010 | Rosenberg |
| 2011/0172607 A1 | 7/2011 | Rosenberg |
| 2011/0301543 A1 | 12/2011 | Rosenberg et al. |
| 2012/0004617 A1 | 1/2012 | Rosenberg et al. |
| 2012/0157925 A1 | 6/2012 | Rosenberg |
| 2012/0157926 A1 | 6/2012 | Rosenberg |
| 2012/0271238 A1 | 10/2012 | Rosenberg |
| 2012/0283644 A1 | 11/2012 | Rosenberg et al. |
| 2013/0066277 A1 | 3/2013 | Rosenberg |
| 2013/0072877 A1 | 3/2013 | Rosenberg |
| 2013/0131599 A1 | 5/2013 | Rosenberg et al. |
| 2014/0007583 A1 | 1/2014 | Rosenberg |
| 2014/0046264 A1 | 2/2014 | Rosenberg |
| 2014/0058331 A1 | 2/2014 | Rosenberg |
| 2014/0207147 A1 | 7/2014 | Rosenberg |
| 2015/0080804 A1 | 3/2015 | Rosenberg |
| 2015/0246208 A1 | 9/2015 | Rosenberg |
| 2016/0074629 A1 | 3/2016 | Rosenberg |
| 2016/0151609 A1 | 6/2016 | Rosenberg |
| 2017/0216563 A1 | 8/2017 | Rosenberg et al. |

FOREIGN PATENT DOCUMENTS

| | | |
|---|---|---|
| WO | WO2004026152 | 4/2004 |
| WO | WO2005039419 | 5/2005 |
| WO | WO2005102438 | 11/2005 |
| WO | WO2007082333 | 7/2007 |
| WO | WO2007103999 | 9/2007 |
| WO | WO2008051810 | 5/2008 |

OTHER PUBLICATIONS

Johnson & Johnson web page printout, "The EndoANCHOR Comparative Summary" printed Sep. 13, 2005, 2 pages.

Johnson & Johnson web page printout, "The EndoANCHOR Features and Benefits" printed Sep. 13, 2005, 2 pages.

Johnson & Johnson web page printout, "The EndoANCHOR Firing Sequences" printed Sep. 13, 2005, 2 pages.

Web Page Printout of Statlock Device, 2 pages.

\* cited by examiner

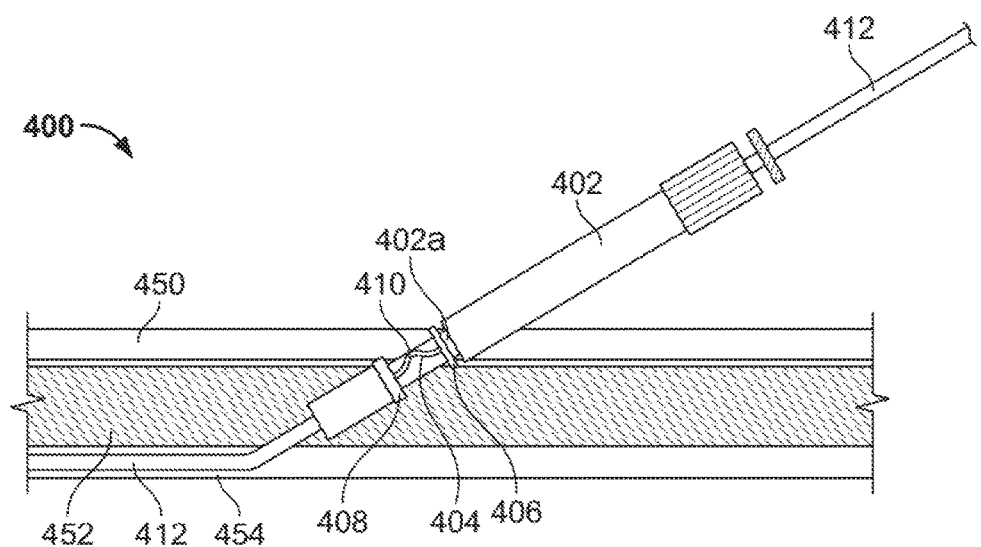
FIG. 13
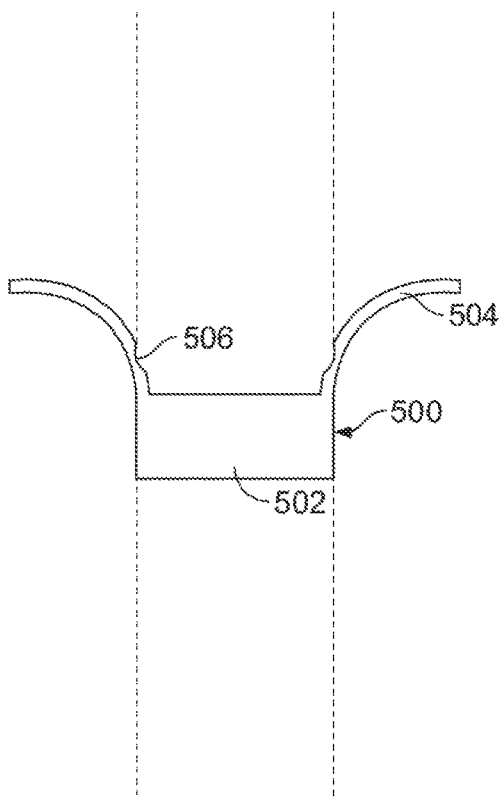
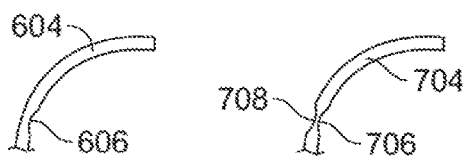
FIG. 14        FIG. 15        FIG. 16

ANCHOR DEVICE AND METHOD

CROSS-REFERENCE TO RELATED APPLICATIONS

This application is a continuation of U.S. application Ser. No. 14/293,125 filed Jun. 2, 2014, which is a continuation of U.S. application Ser. No. 13/211,625 filed on Aug. 17, 2011 (now U.S. Pat. No. 8,771,232), which is a continuation of U.S. application Ser. No. 12/553,555 filed on Sep. 3, 2009 (now U.S. Pat. No. 8,016,813), which is a division of U.S. application Ser. No. 11/372,283 filed on Mar. 9, 2006 (now U.S. Pat. No. 8,016,794), the contents of these prior applications being incorporated herein by reference.

TECHNICAL FIELD

This document relates to an anchor device, such as an anchor device for use in temporary placement of a catheter or other medical device.

BACKGROUND

Venous, arterial, and body fluid drainage catheters are commonly used by physicians. For example, such catheters may be used to temporarily gain access to the vascular system for introducing pharmaceutical agents, for nutrition or fluids, for hemodynamic monitoring, and for blood draws. Alternatively, catheters can be used for drainage of fluid collections and to treat infection. Following introduction into the patient, the catheter is typically secured to the patient using a tape patch or by suturing an attached hub to the skin.

SUMMARY

Some embodiments of an anchor device may include a bendable anchor mechanism that is deployable in a subcutaneous layer to releasably secure the anchor device to a patient's body. Certain embodiments of the anchor mechanism may include one or more barbs that flexibly bend in response to an insertion or removal force. As such, the anchor mechanism may be inserted into a subcutaneous layer, and removed from the subcutaneous layer, without the need for a separate actuation device to extend or retract the barbs.

In some embodiments, an anchor device may include an elongate body having a body wall that at least partially defines a lumen. The device may also include a subcutaneous anchor mechanism coupled to the elongate body. The subcutaneous anchor mechanism may have one or more non-retractable barbs that extend away from the body wall when in a deployed orientation in a subcutaneous layer. The non-retractable barbs may be flexibly bendable to a removal orientation when the anchor mechanism is withdrawn from the subcutaneous layer and out through a dermis layer. In one aspect, the elongate body may be a catheter configured to provide access to a patient's body. In another aspect, the elongate body may be a sleeve body configured to slidably receive a catheter or a medical instrument.

In some embodiments, a subcutaneous anchor mechanism may include a base attachable to a medical device. The mechanism may also include at least one non-retractable barb coupled to the base. The non-retractable barb may extend from the base such that, when the base is attached to the medical device, the non-retractable barb extends away from the medical device when in a deployed orientation in a subcutaneous layer. The non-retractable barb may be flexibly bendable to a removal orientation when the non-retractable barb is withdrawn from the subcutaneous layer and out through a dermis layer.

In some embodiments, an anchor device may include an elongate body having a body wall that at least partially defines a lumen. The device may also include means for subcutaneously anchoring the elongate body to a portion of skin. The subcutaneous anchor means may be coupled to the elongate body. The subcutaneous anchor means may include means for non-retractably withdrawing from a deployed orientation in a subcutaneously layer to a bent orientation when passing through a dermis layer. In one aspect, the means for non-retractably withdrawing may comprise one or more non-retractable barbs that extend away from the body wall when deployed in the subcutaneous layer.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 10 is a side view of an embodiment of an anchor mechanism.

FIG. 11 is a side view of an alternative embodiment of an anchor mechanism.

FIG. 12 is a side view of an alternative embodiment of an anchor mechanism.

FIG. 13 is a side view of the anchor sleeve of FIG. 12 and a catheter advanced into a patient's blood vessel.

FIG. 14 is a side view of a further embodiment of an anchor mechanism, attached to a medical device shown in phantom lines.

FIG. 15 is a side view of an embodiment of a barb of an anchor mechanism.

FIG. 16 is a side view of a further embodiment of a barb of an anchor mechanism.

Like reference symbols in the various drawings indicate like elements.

DETAILED DESCRIPTION OF ILLUSTRATIVE EMBODIMENTS

Figure 1:
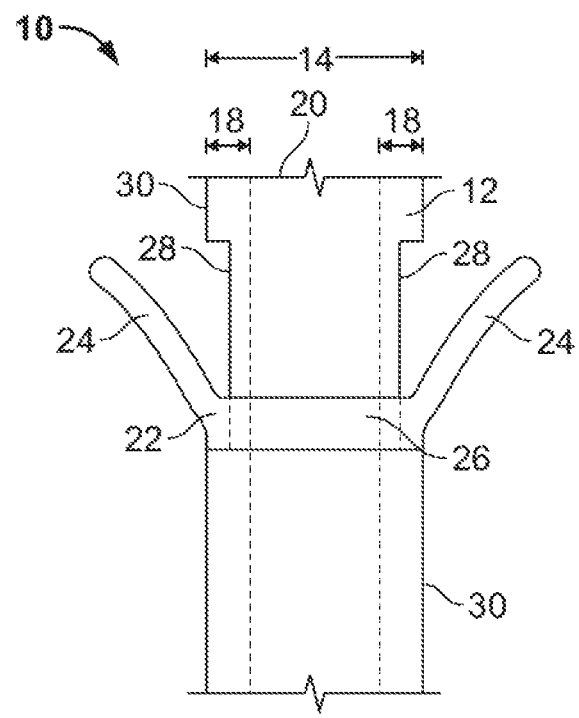
FIG. 1 is a side view of an embodiment of an anchor catheter having an anchor mechanism attached to the catheter.
Figure 2:
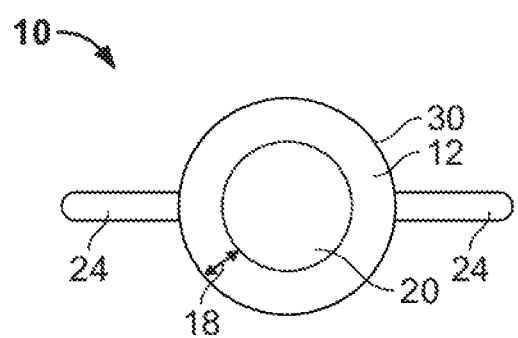
FIG. 2 is an end view of the anchor catheter shown in FIG. 1.

Referring to FIGS. 1-2, some embodiments of an anchor catheter 10 may include an anchor mechanism in an unstressed configuration prior to being introduced into a patient. The anchor catheter 10 may include a catheter body 12 to which the anchor mechanism 22 is coupled. The anchor mechanism 22 may include a base 26 which extends at least partially around the catheter body 12 and includes one or more barbs 24. The base 26 may be permanently or releasably coupled to the catheter body 12 using, for example, adhesive, ultrasonic welding, compression fit, frictional engagement, internal engagement spikes, or the like. In this embodiment, the anchor mechanism 22 includes two barbs 24. At least the barb 24, and in some embodiments the entire anchor mechanism 22, is made from a nitinol material which has been processed to exhibit superelasticity below or at about a normal human body temperature, such as below or at about 37 degrees C. These superelasticity characteristics permit the barbs 24 to flex during insertion into a subcutaneous region, to flex during removal from the patient's skin, and (in some circumstances) to return to its unstressed shape. In these embodiments, the barbs 24 may be non-retractable so that such flexing action may occur from the insertion and removal force applied to the catheter 12 or other medical device, without the need for a separate actuation device to fully retract the barbs 24 into a cavity.

In one embodiment, the anchor mechanism 22 may be formed from a length of nitinol tubing from which a portion has been cut away using laser cutting, electro chemical machining (ECM), electrical discharge machining (EDM), water jet or other machining process. As such, the base 26 may be integrally formed with the barbs 24. In these embodiments, the barbs 24 may be thermo-mechanically trained to extend away from the plane of the outer wall 30 of the catheter 12, as described in greater detail below. It should be understood that, in the embodiments in which the barbs 24 comprise a nitinol material, the barbs 24 may be formed from a length of nitinol wire or from a sheet of nitinol material. The nitinol material may comprise, for example, Nickel Titanium (NiTi), Niobium Titanium (NbTi), or the like. Alternatively, at least the barbs 24, and in some circumstances the entire anchor mechanism 22, may comprise a metal material such as stainless steel, spring steel, titanium, MP35N and other cobalt alloys, or the like. In another embodiment, some or all of the anchor mechanism 22 may comprise a bio-compatible polymer material that is configured to elastically flex during insertion into a subcutaneous region and configured to elastically flex or plastically deform during removal from the patient's skin. For example, the anchor mechanism can be thermoformed or otherwise molded from a PEEK material, a polyurethane material, a polyethylene material, a polyimide material, or another bio-compatible polymer material. In some embodiments, the barbs 24 may have grooves or notches formed therein to facilitate the proper flexing or deformation during insertion into the subcutaneous region or removal from the patient's skin, as described in more detail below.

Still referring to FIGS. 1-2, the barbs 24 may extend away from the plane of the outer wall 30 of the catheter body 12. The catheter body 12 may define a catheter wall outer diameter 14 and thickness 18 are defined, as is a catheter lumen 20. As shown in FIG. 1, some embodiments of the catheter body 12 may comprise a wall pocket 28 to receive the barbs 24 in the event the barbs forced against the outer wall 30. In these embodiments, the wall pocket 28 may serve to reduce the likelihood of trauma to the patient's skin during insertion by providing a space to accommodate one or more barbs 24.

Figure 3:
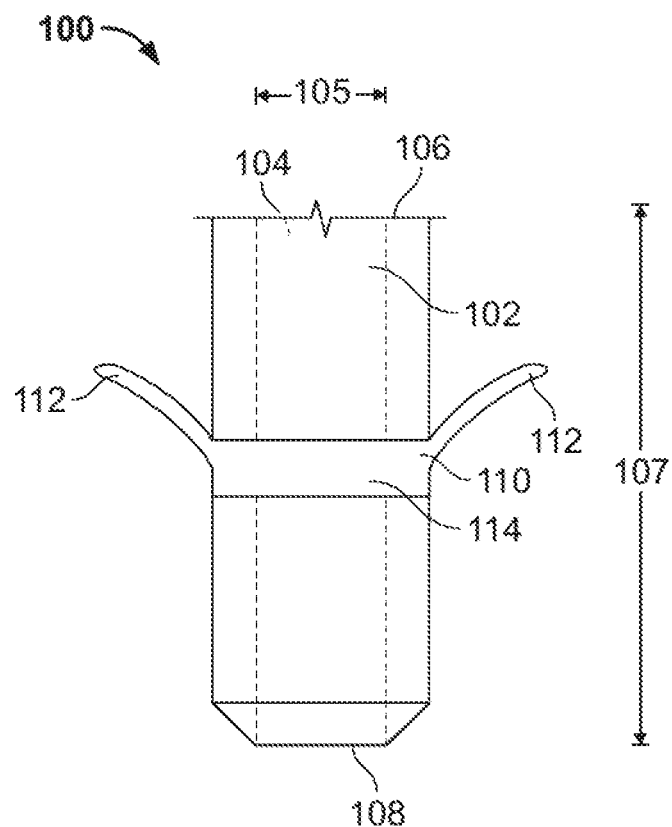
FIG. 3 is a side view of an embodiment of an anchor sleeve having an anchor mechanism attached to the anchor sleeve, without a catheter or other device inserted therein.
Figure 3A:
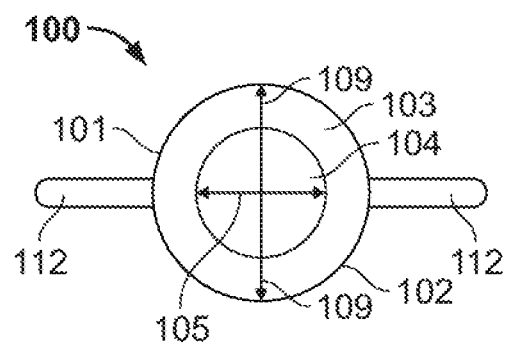
FIG. 3A is an end view of the anchor sleeve shown in FIG. 3.
Figure 7:
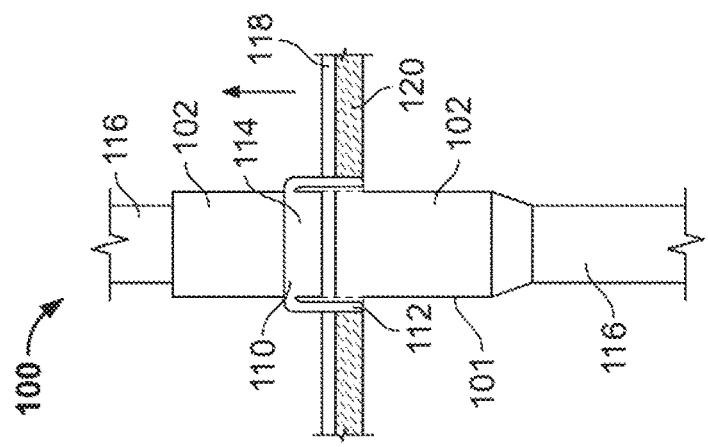
FIG. 7 is a side view of the anchor sleeve shown in FIG. 3 during insertion into a patient.

Referring to FIGS. 3-3A, some embodiments of an anchor sleeve 100 may include an anchor mechanism 110 coupled thereto. The anchor sleeve 100 may comprise a sleeve body 102 to slidably receive a medical device (e.g., instrument, catheter, needle, etc.) therethrough. The anchor sleeve 100 may define a longitudinal dimension 107, a proximal end 106, a distal end 108 and a lumen 104. The lumen 104 may define an inner diameter 105 that is shaped and sized to slidably receive a catheter 116 (FIG. 7). Some embodiments of the sleeve body 102 may comprise a wall pocket (not shown in FIG. 3) in the outer wall 101 to receive the barbs 112 in the event the barbs 112 are forced against the outer wall 101.

The anchor mechanism 110 may include a base 114 that at least partially extends around the outer diameter 109 of the sleeve body 102. The anchor mechanism 110 may include one or more barbs 112 that extend from the plane of the outer wall 101 of the sleeve body 102. In this embodiment, the anchor mechanism 110 includes two barbs 112. The one or more barbs 112, and in some embodiments the entire anchor mechanism 110, can be made from nitinol material which has been processed to exhibit superelasticity below or at about a normal human body temperature, such as below or at about 37 degrees C. Such superelasticity characteristics permit the barbs 112 to flex during insertion into a subcutaneous region, to flex during removal from the patient's skin, and (in some circumstances) to return to its unstressed shape. In these embodiments, the barbs 112 may be non-retractable so that such flexing action may occur from the insertion and removal force applied to the sleeve body 102 or other medical device, without the need for a separate actuation device to fully retract the barbs 112 into a cavity. As previously described, the anchor mechanism 110 may be formed from a length of nitinol tubing from which a portion has been cut away using laser cutting, ECM, EDM, water jet or other machining process. Also as previously described, the barbs 112 may be thermo-mechanically trained to extend away from the plane of the outer wall 101 of the sleeve body 102. It should be understood that, in the embodiments in which the barbs 112 comprise a nitinol material, the barbs 112 may be formed from a length of nitinol wire or from a sheet of nitinol material. Alternatively, at least the barbs 112, and in some circumstances the entire anchor mechanism 110, may comprise a metal material such as stainless steel, spring steel, titanium, MP35N and other cobalt alloys, or the like.

In another embodiment, some or all of the anchor mechanism 110 may comprise a bio-compatible polymer material that is configured to elastically flex during insertion into a subcutaneous region and configured to elastically flex or plastically deform during removal from the patient's skin. For example, the anchor mechanism may be thermoformed or otherwise molded from a PEEK material, a polyurethane material, a polyethylene material, a polyimide material, or another bio-compatible polymer material. As described in more detail below, the barbs 112 may have grooves or notches formed therein to facilitate the proper flexing or deformation during insertion into the subcutaneous region or removal from the patient's skin.

Figure 6:
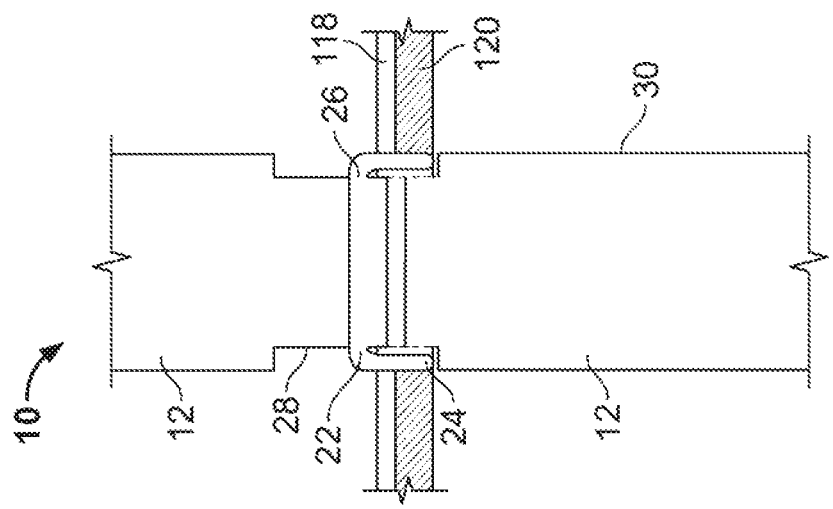
FIG. 6 is a side view of the anchor catheter shown in FIG. 1 during removal from the patient.
Figure 5:
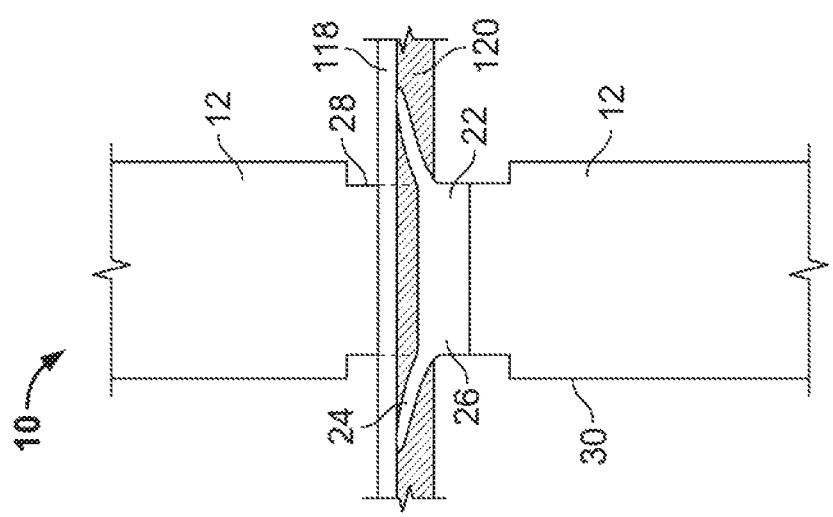
FIG. 5 is a side view of the anchor catheter shown in FIG. 1 following insertion into a patient.
Figure 4:
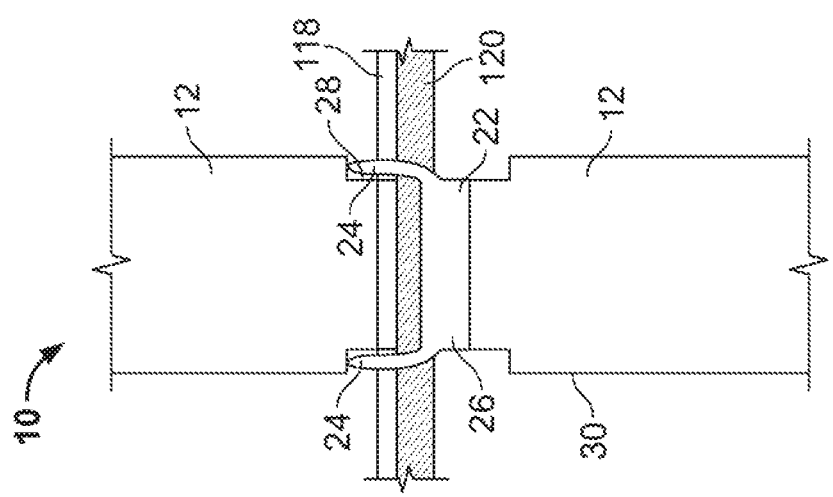
FIG. 4 is a side view of the anchor catheter shown in FIG. 1 during insertion into a patient.

Referring to FIGS. 4-6, the anchor catheter 10 previously described in connection with FIGS. 1-2 may be introduced into a patient so that the anchor mechanism 22 may releasably secure the catheter body 12 to the patient. As previously described, the insertion force applied to the catheter body 12 or other medical device may cause at least a portion of the anchor mechanism 22 to flex during insertion into a subcutaneous region, and the removal force applied to the catheter body 12 or other medical device may cause at least a portion of the anchor mechanism 22 to flex or deform during removal from the patient's skin. Thus, the anchor mechanism 22 may be self-actuated without the need for a separate actuation device to extend or retract the barbs 24.

As shown in FIG. 4, the anchor catheter 10 may be introduced through a patient's skin prior to commencement of a medical procedure or other treatment. For example, the anchor catheter 10 may penetrate the dermis 118 and subcutaneous layer 120 through a small incision made by a physician, and in some cases a dilation instrument may be used to advance the catheter 10 toward the targeted vessel. As a result of an insertion force applied to the catheter body 12 by the physician, the barbs 24 may be temporarily flexed from their unstressed configuration (as shown, for example, in FIG. 1) to a proximally oriented configuration in which the barbs 24 extend substantially in a direction along the outer wall 30 of the catheter body 12. Such flexing action permits at least a portion of the anchor mechanism 22 to enter through the incision with a reduced likelihood of traumatizing the skin around the incision.

Referring to FIG. 5, when the anchor catheter 10 is introduced into the patient and during the treatment period, the catheter body 12 penetrates the dermis 118 and subcutaneous layer 120. After the barbs 24 have passed through the dermis 118, the barbs 24 can return partially or fully toward the unstressed configuration (as shown, for example, in FIG. 1) so as to deploy within the subcutaneous layer 120. For example, the subcutaneous layer 120 may comprise fatty tissue in which the barbs 24 can move in a sweeping arcuate motion away from the catheter body 12. Such deployment in the subcutaneous layer 120 may releasably secure the anchor catheter 10 to the patient's body for the duration of the medical procedure. In this embodiment, the barbs 24 extend away from the outer wall 30 of the catheter body 12 with an curvature so that the tips of the barbs 24 are not necessarily pointed at the underside of the dermis 118. Such a configuration may be accomplished, for example, by inserting the barbs 24 further into the subcutaneous layer 120 and then moving the barbs with a slight pulling motion to permit the barbs to sweep outwardly from the catheter body 12. It should be understood that, due to the vagaries of human anatomy and differing inward and outward forces during treatment, in some embodiments the orientation and position of the deployed barbs 24 may vary when deployed in the subcutaneous layer 120. In some embodiments, the anchor mechanism 22 may provide a holding force of about 1 lb. or greater, depending upon the medical procedure being performed, the materials of the anchor mechanism 22 (e.g., a nitinol material may be "programmed" to have particular bending forces, as described in more detail below), the geometry of the barbs 24, and other factors. For example, the anchor mechanism 22 may provide a holding force of about 1 lb to about 50 lbs, about 1 lb to about 20 lbs, about 1 lb to about 5 lbs, or about 2 lbs to about 3 lbs.

Referring to FIG. 6, the anchor catheter 10 may be removed from the patient following completion of medical procedure. As a result of a removal force applied to the catheter body 12 that overcomes the holding force of the anchor mechanism 22, the barbs 24 may be temporarily flexed from their deployed configuration (as shown, for example, in FIG. 5) to a distally oriented configuration in which the barbs 24 extend substantially in a direction along the outer wall 30 of the catheter body 12. Such flexing action permits at least a portion of the anchor mechanism 22 to exit through the incision in the patient's skin with a reduced likelihood of traumatizing the skin around the incision. For example, the barbs 24 may have a curved configuration in which the tips do not point directly at the dermis 118) when deployed in the subcutaneous layer 120 (refer, in one example, to FIG. 5). As such, the removal force causes the barbs 24 to flex (rather than substantially tear through the underside of the dermis 118) in a generally sweeping motion toward the distally oriented configuration (refer, in one example, to FIG. 6). In the embodiments in which the barbs 24 comprise a nitinol material exhibiting superelastic characteristics, the barbs 24 can return toward the unstressed configuration (as shown, for example in FIG. 1) following removal of the anchor mechanism 22 from the skin. In some alternative embodiments, the barbs 24 may comprise a biocompatible polymer material that is elastically or plastically deformed into the distally oriented configuration (as shown, for example, in FIG. 6) as a result of the removal force applied to the catheter body 12.

Figure 8:
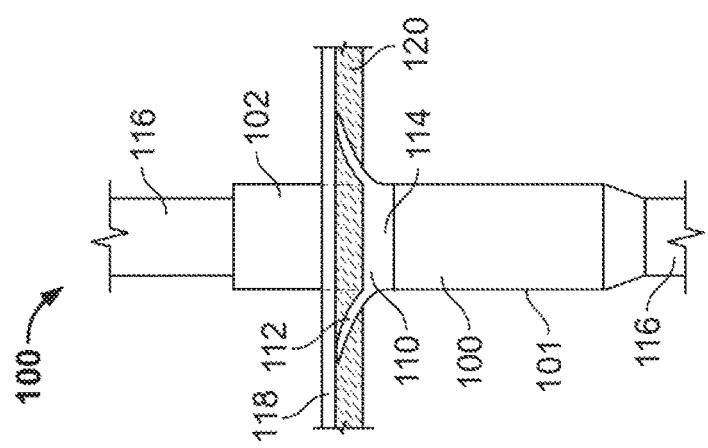
FIG. 8 is a side view of the anchor sleeve shown in FIG. 3 following insertion into a patient.
Figure 9:
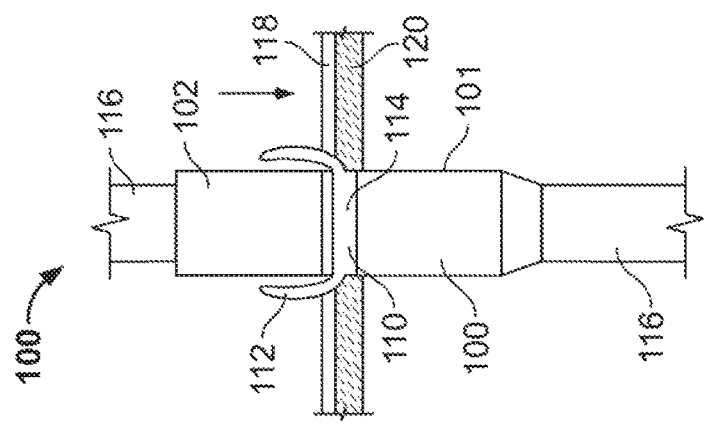
FIG. 9 is a side view of the anchor sleeve shown in FIG. 3 during removal from the patient.

Referring to FIGS. 7-9, the anchor sleeve 100 previously described in connection with FIGS. 3-3A may be introduced into a patient so that the anchor mechanism 110 may releasably secure the sleeve body 102 to the patient. As previously described, the insertion force applied to the sleeve body 102 or other medical device may cause at least a portion of the anchor mechanism 110 to flex during insertion into a subcutaneous region, and the removal force applied to the sleeve body 102 or other medical device may cause at least a portion of the anchor mechanism 110 to flex or deform during removal from the patient's skin. Thus, the anchor mechanism 110 may be self-actuated without the need for a separate actuation device to extend or retract the barbs 112.

As shown in FIG. 7, the anchor sleeve 100 may be introduced into a patient prior to commencement of medical procedure or other treatment. For example, the anchor sleeve 100 may penetrate the dermis 118 and the subcutaneous layer 120 through a small incision made by a physician. As a result of an insertion force applied to the sleeve body 102 by the physician, the barbs 112 may be temporarily flexed from their unstressed configuration (as shown, for example, in FIG. 1) to a proximally oriented configuration in which the barbs 112 extend substantially in a direction along the outer wall 101 of the sleeve body 102. Such flexing action permits at least a portion of the anchor mechanism 110 to enter through the incision with a reduced likelihood of traumatizing the skin around the incision. During the medical procedure or other treatment, a medical device such as a catheter 116 may be slidably inserted into the anchor sleeve 100. Alternatively, the medical device such as the catheter 116 may be inserted into the anchor sleeve 100 prior to introducing the anchor sleeve into the patient.

Referring to FIG. 8, when the anchor sleeve 100 is introduced into the patient and during the treatment period, the sleeve body 102 penetrates the dermis 118 and subcutaneous layer 120. After the barbs 112 have passed through the dermis 118, the barbs 112 can return partially or fully toward the unstressed configuration (as shown, for example, in FIG. 3) so as to deploy within the subcutaneous layer 120. As previously described, the subcutaneous layer 120 may comprise fatty tissue in which the barbs 112 can move in a sweeping arcuate motion away from the sleeve body 102. Such deployment in the subcutaneous layer 120 may releasably secure the anchor sleeve 100 to the patient's body for the duration of the medical procedure. In this embodiment, the barbs 112 extend away from the outer wall 101 of the sleeve body 102 with a curvature so that the tips of the barbs 112 are not necessarily pointed at the underside of the dermis 118. Such a configuration may be accomplished, for example, by inserting the barbs 112 further into the subcutaneous layer 120 and then moving the barbs with a slight pulling motion to permit the barbs 112 to sweep outwardly from the sleeve body 102. It should be understood that, due to the vagaries of human anatomy and differing inward and outward forces during treatment, in some embodiments the orientation and position of the deployed barbs 112 may vary when deployed in the subcutaneous layer 120. In some embodiments, the anchor mechanism 110 may provide a holding force of about 1 lb. or greater, depending upon the medical procedure being performed, the materials of the anchor mechanism 110 (e.g., a nitinol material may be "programmed" to have particular bending forces, as described in more detail below), the geometry of the barbs 112, and other factors. For example, the anchor mechanism 110 may provide a holding force of about 1 lb to about 50 lbs, about 1 lb to about 20 lbs, about 1 lb to about 5 lbs, or about 2 lbs to about 3 lbs.

Referring to FIG. 9, the anchor sleeve 100 may be removed from the patient following completion of medical procedure. As a result of a removal force applied to the sleeve body 102 by the physician, the barbs 112 may be temporarily flexed from their deployed configuration (as shown, for example, in FIG. 8) to a distally oriented configuration in which the barbs 112 extend substantially in a direction along the outer wall 101 of the catheter body 102. Such flexing action permits at least a portion of the anchor mechanism 110 to exit through the incision in the patient's with a reduced likelihood of traumatizing the skin around the incision. For example, the barbs 112 may have a curved configuration in which the tips do not point directly at the dermis 118) when deployed in the subcutaneous layer 120 (refer, in one example, to FIG. 8). As such, the removal force causes the barbs 112 to flex (rather than substantially tear through the underside of the dermis 118) in a generally sweeping motion toward the distally oriented configuration (refer, in one example, to FIG. 9). In the embodiments in which the barbs 112 comprise a nitinol material exhibiting superelastic characteristics, the barbs 112 can return toward the unstressed configuration (as shown, for example in FIG. 3) following removal of the anchor mechanism 110 from the skin. In some alternative embodiments, the barbs 112 may comprise a biocompatible polymer material that is elastically or plastically deformed into the distally oriented configuration (as shown, for example, in FIG. 9) as a result of the removal force applied to the sleeve body 102.

Figures 10, 11, 12:
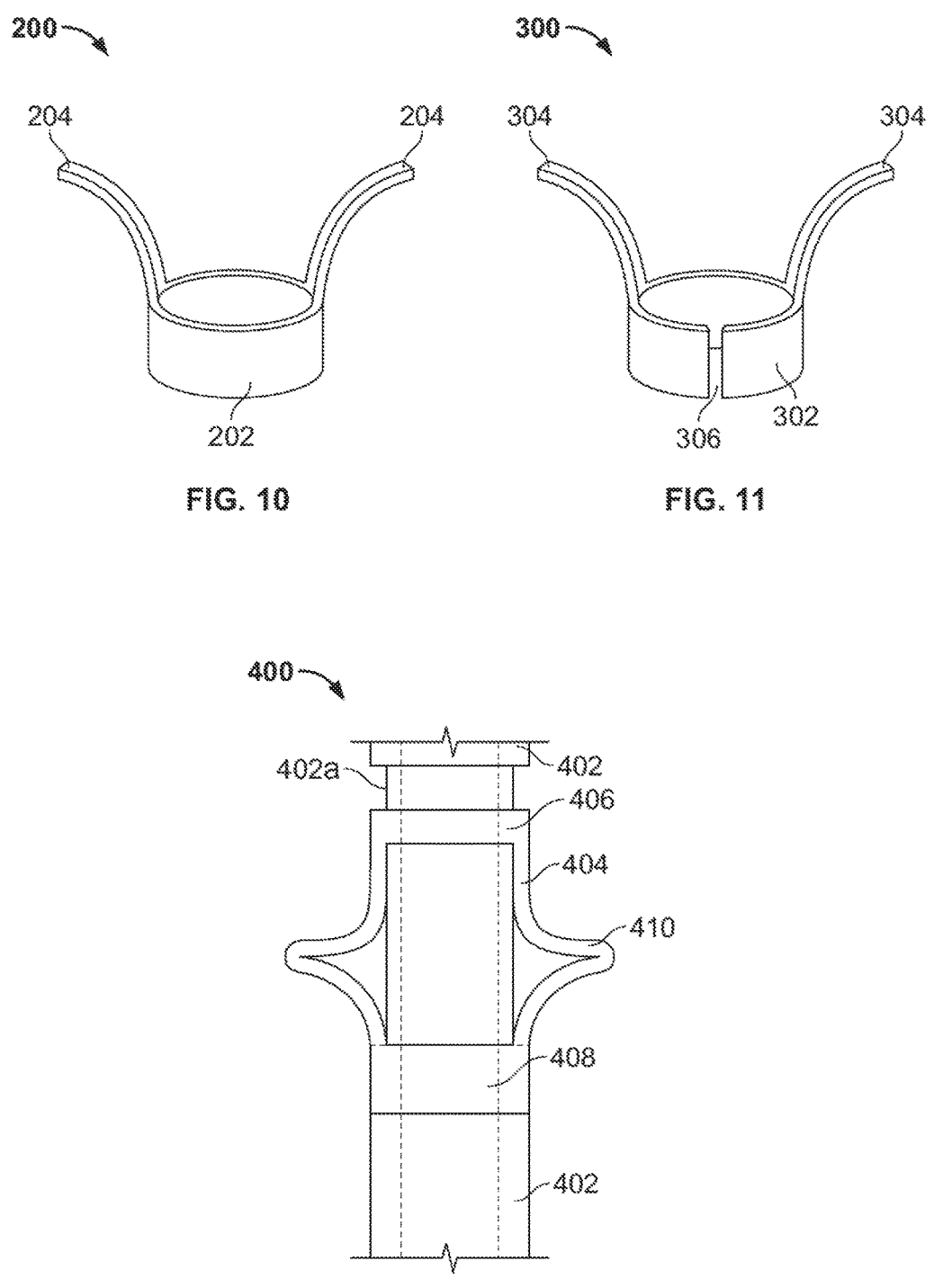

Referring now to FIG. 10, some embodiments of an anchor mechanism 200 may be separately attachable to a catheter body, a sleeve body, or another medical device that may require securing to a patient during a treatment period. The anchor mechanism 200 may include a base 202 and one or more barbs 204. In this embodiment, the anchor mechanism includes two barbs 204 that extend away from one another. As previously described, some embodiments of the anchor mechanism 200 may be formed from a length of nitinol tubing from which a portion has been cut away using laser cutting, ECM, EDM, water jet or machining process. Also the barbs 204 may be thermo-mechanically trained to extend away from the plane of an outer wall (not shown in FIG. 10) of the catheter body, sleeve body, or other medical device.

Referring to FIG. 11, some embodiments of an anchor mechanism 300 may include a base 302 that is not continuous and has a gap 306. The anchor mechanism may be separately attachable to a catheter body, a sleeve body, or another medical device that may require securing to a patient during a treatment period. The anchor mechanism 300 may also include one or more barbs 304, and in this embodiment, the anchor mechanism 300 includes two barbs 304 that extend away from one another. The gap 306 may permit the base 304 to be spread apart so as to wrap around some portion of the catheter body, sleeve body, or other medical device prior to introduction of the medical device into the patient. As previously described, some embodiments of the anchor mechanism 300 may be formed from a length of nitinol tubing from which a portion has been cut away using laser cutting, ECM, EDM, water jet or other machining process. Also the barbs 304 may be thermo-mechanically trained to extend away from the plane of an outer wall (not shown in FIG. 10) of the catheter body, sleeve body, or other medical device.

The anchor mechanisms 200 and 300 may operate in a manner similar to the embodiments shown in FIGS. 1-9. For example, the barbs 204, 304 may be moved from the unstressed configuration (as shown, for example, in FIG. 10 or 11) to a proximally oriented configuration (similar to that shown, for example, in FIG. 4 or 7) in response to an insertion force during introduction into the patient's skin through an incision. In another example, when the attached catheter body, sleeve body, or other medical device is in the treatment position (similar to that shown, for example, in FIG. 5 or 8), the barbs 204, 304 may return toward the unstressed configuration so as to deploy within the subcutaneous layer 120. In a further example, the barbs 204, 304 may be moved from the unstressed configuration (as shown, for example, in FIG. 10 or 11) to a distally oriented configuration (similar to that shown, for example, in FIG. 6 or 9) in response to a removal force during removal from the patient's skin.

Referring to FIG. 12, some embodiments of an anchor catheter 400 (or sleeve) may include anchor mechanism 404 having at least one atraumatic loop 410. The anchor mechanism 404 may be coupled to a catheter body 402 (or a sleeve body) of the anchor catheter 400. The loop 410 may not have a free end and instead may be attached at one end to a slidable base 406 and the other end to a second base 408, which may be fixed or slidable. In this embodiment, the second base 408 is fixedly coupled to the catheter body 402. As shown in FIG. 12, the loop 410 may have a non-symmetric shape in which the first end (extending toward the proximal base 406) has a sharper curvature when in an unstressed configuration. The catheter body 402 may define a neck portion 402a having a reduced diameter extending to a shoulder so that the slidable base 406 may slide along the neck portion 402a and may abut the shoulder. Thus, the slidable base 406 of the anchor mechanism 404 may move in the longitudinal direction during insertion and removal of the anchor catheter 400. It should be understood that the neck portion 402a may be long enough such that the slidable base 406 may be moved a sufficient distance away from the second base 408 so that loop 410 does not protrude outward past the outer diameter of the catheter body 402. In such embodiments, the slidable base 406 and the second base 408 can be disposed along the neck portion 402a and may be configured to not protrude beyond the outer dimension of the catheter body 402.

At least the atraumatic loop 410, and in some embodiments the entire anchor mechanism 404, is made from nitinol material which has been processed to exhibit superelasticity below or at about a normal human body temperature, such as below or at about 37 degrees C. Such superelasticity characteristics permit the atraumatic loop 410 to flexibly adjust during insertion into a subcutaneous region and to flexibly adjust during removal from the patient's skin. In some circumstances, such flexing action may occur from the insertion and removal force applied to the catheter body 402 or other medical device, without the need for a separate actuation device to adjust the atraumatic loop 410. As previously described, some embodiments of the anchor mechanism 404 may be formed from a length of nitinol tubing from which a portion has been cut away using laser cutting, ECM, EDM, water jet or other machining process. Also, the atraumatic loop 410 may be thermo-mechanically trained to extend away from the neck portion 402a. It should be understood that, in the embodiments in which the loop 410 comprises a nitinol material, the loop 410 may be formed from a length of nitinol wire or from a sheet of nitinol material. In some alternative embodiments, the atraumatic loop 410 may comprise a biocompatible polymer material that is flexibly adjustable during insertion and removal of the anchor mechanism 404. It should be understood that a similar anchor mechanism 404 may be coupled to an anchor sleeve (not shown in FIG. 12) in a similar manner to the anchor catheter 400.

Referring to FIG. 13, the anchor catheter 400 may be introduced into a patient so that the anchor mechanism 404 may releasably secure the catheter body 402 to the patient. As previously described, the insertion force applied to the catheter body 402 or other medical device may cause the atraumatic loop 410 to flex during insertion into a subcutaneous region. As shown in FIG. 13, the atraumatic loop 410 may shift from its unstressed configuration (as shown, for example, in FIG. 12) to an extended configuration so as to fit through a small incision made in the patient's skin. This adjustment of the atraumatic loop 410 causes the slidable base 406 to shift toward the shoulder of the neck portion 402a. For example, the loop 410 may shift to the extended configuration when the insertion force causes the patient's dermis to act upon the second end of the loop 410. Alternatively, a physician may pull upon the slidable based 406 to force the loop into the extended configuration during insertion of the loop into the subcutaneous layer 452.

After the anchor mechanism 404 is passed into the subcutaneous layer 452, the atraumatic loop 410 may return towards its unstressed configuration (as shown, for example, in FIG. 12) so as to deploy the atraumatic loop 410 in the subcutaneous layer 452. In response to a removal force applied to the catheter body 402, the atraumatic loop 410 may flex to the extended configuration during removal from the patient's skin. In one example, a physician may pull upon the slidable based 406 to force the loop into the extended configuration during removal of the loop from the subcutaneous layer 452. Thus, the anchor mechanism 404 may be self-actuated without the need for a separate actuation device to adjust the atraumatic loop 410. Further, the atraumatic loop 410 may not include exposed tip regions, thereby facilitating the removal of the anchor mechanism 404 with a reduced likelihood of traumatizing the skin around the incision.

Referring to FIGS. 14-16, some embodiments of an anchor mechanism 500 may include a barb 504 having a notch or other hinge configuration 506 to facilitate the adjustment of the barb 504. The anchor mechanism 500 may include a base 502 and one or more barbs 504. The base 502 at least partially extends around the attached catheter body, sleeve body, or other medical device. The hinge 506 may be formed proximate the point of attachment between the base 502 and barb 504 so as to facilitate movement of the barb 504 during introduction and removal of the attached catheter body, sleeve body, or other medical device. In this embodiment shown in FIG. 14, the hinge 506 is formed on the inner side of the barb 504 (e.g., toward the attached medical device). FIG. 15 shows an alternative embodiments of a barb 604 having the hinge 606 formed on the outer surface (e.g., away from the attached medical device). FIG. 16 shows yet another embodiment of a barb 704 having at least a first hinge 706 and a second hinge 708 formed on opposite sides of the barb 704. In these embodiments, one function of the hinge 506, 606, 706, 708 may be to provide a degree of control or predictability as to the location and the threshold force level at which the barb 504, 604, 704 will flex during introduction and removal of the attached medical device. In some embodiments, at least the barbs 504, 604, 704, and in some circumstances the anchor mechanism 502, may comprise a biocompatible polymer material, such as PEEK material, polyurethane material, polyethylene material, polyimide material, or another bio-compatible polymer material. In other embodiments, at least the barbs 504, 604, 704, and in some circumstances the anchor mechanism 502, may comprise a metal material such as nitinol, stainless steel, spring steel, titanium, MP35N and other cobalt alloys, or the like. Alternatively, at least the barbs 504, 604, 704, and in some circumstances the anchor mechanism 502, may comprise a composite material such as polymer-coated nitinol or another biocompatible composite material.

Figure 17:
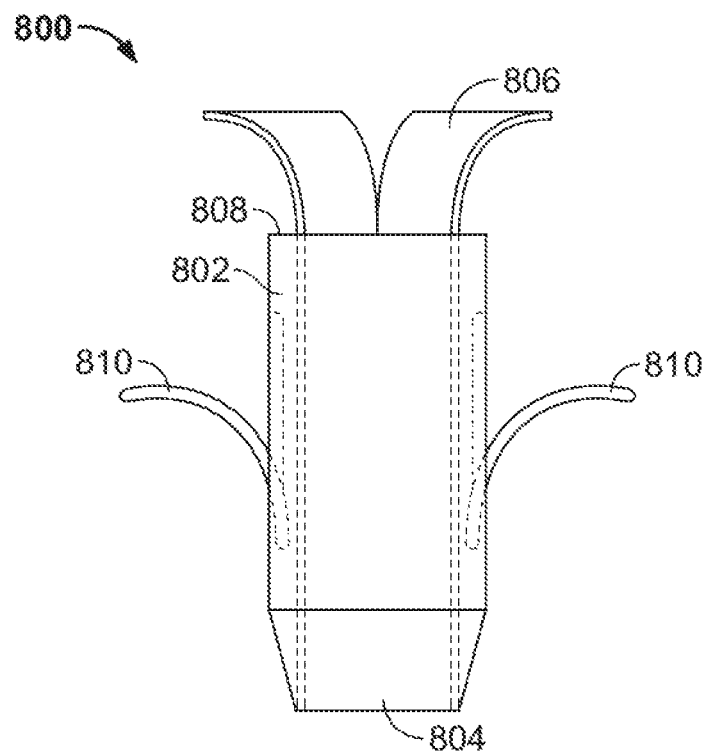
FIG. 17 is a side view of an alternative embodiment of an anchor sleeve including an adhesive portion used to secure an inserted catheter.
Figure 18:
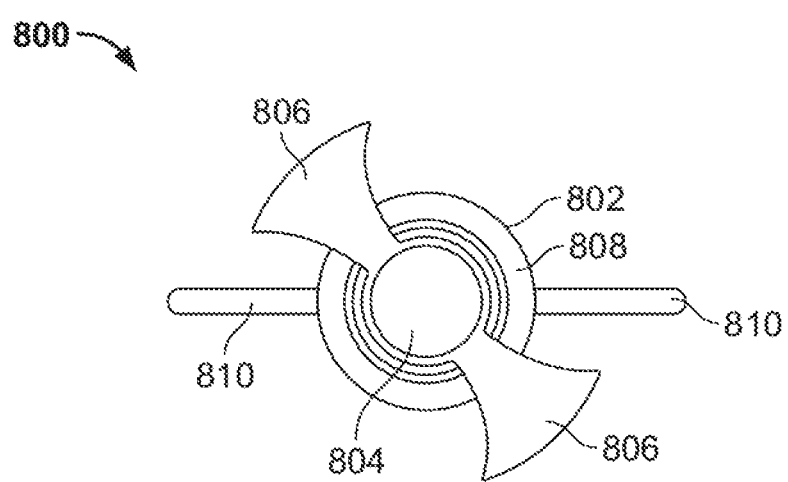
FIG. 18 is a top view of the anchor sleeve shown in FIG. 17.

Referring to FIGS. 17-18, some embodiments of an anchor sleeve 800 (or, alternatively, an anchor catheter) may include an adhesive portion 806 to secure a catheter or other medical device that is slidably engaged with the lumen 804. The anchor sleeve 800 includes a sleeve body 802 that defines a lumen 804. The lumen 804 may be a generally cylindrical conduit extending the length of the sleeve body 802. The adhesive portion 806 may be used to secure the position of a catheter (or other medical device) that is inserted into the anchor sleeve 800 either before or after the anchor sleeve 800 has been introduced into the patient. In this embodiment, the adhesive portion 806 may include an adhesive layer that is revealed after removing a peel-away liner.

The sleeve body 802 may include a wall 808 having a thickness sufficient to receive at least a portion of one or more barbs 810. As such, the barbs 802 may be embedded into the wall 808 of the sleeve body 802. In this embodiment, the stem portion of the barbs 810 may be integrally molded with the wall 808, may be adhered into the wall 808, or may be frictionally engaged within a cavity formed in the wall 808. The barbs may be formed to have a curvature so that the body of each barb 810 may extend away from the outer surface of the wall 808. In some embodiments, each barb 810 is made from a nitinol material which has been processed to exhibit superelasticity below or at about a normal human body temperature, such as below or at about 37 degrees C. Such superelasticity characteristics permit each barb 810 to flexibly adjust during insertion into a subcutaneous region and to flexibly adjust during removal from the patient's skin. In some circumstances, such flexing action may occur from the insertion and removal force applied to the sleeve body 802 or other medical device, without the need for a separate actuation device to extend or retract the barbs 810.

Figure 19:
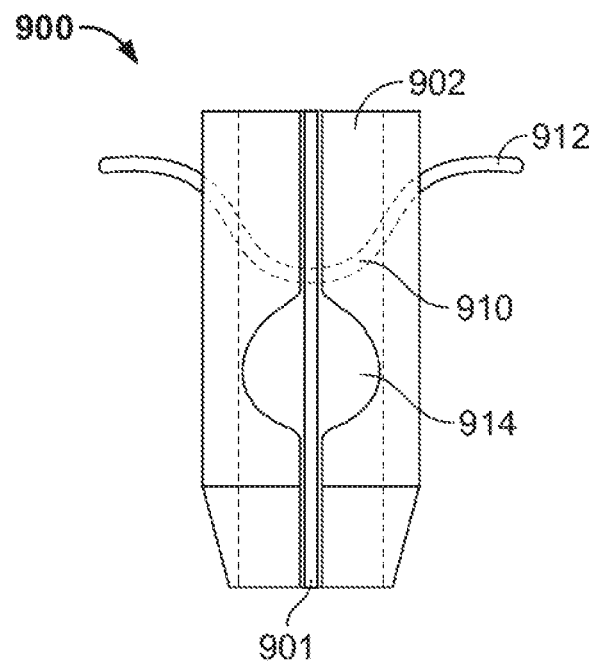
FIG. 19 is a side view of an embodiment of a split anchor sleeve having adhesive tabs extending from the split.
Figure 20:
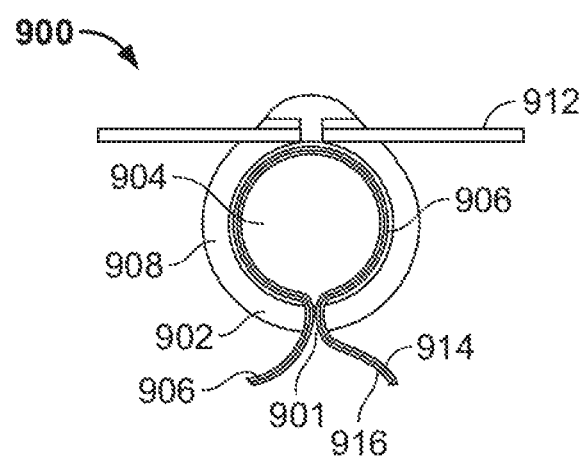
FIG. 20 is a top end view of the anchor sleeve shown in FIG. 19.

Referring to FIGS. 19-20, some embodiments of an anchor sleeve 900 may include a longitudinal gap 901 extending from the proximal end. The longitudinal gap 901 may permit an adhesive portion to be removable received in the lumen 904 of the sleeve body 902. Further, in some circumstances, the longitudinal gap 904 may permit the sleeve body 902 to be temporarily spread apart to wrap at least partially around a catheter or other medical device.

In some embodiments, an anchor mechanism 910 may be coupled to the sleeve body 902 by integrally molding with a sleeve body wall 908, adhering into the sleeve body wall 908, or frictionally engaging a cavity formed in the sleeve body wall 908. The anchor mechanism 910 may comprise a nitinol material that has been processed to exhibit superelastic or shape memory characteristics, a stainless steel material, a spring steel material, titanium, MP35N and other cobalt alloys, a biocompatible polymer material, or composites thereof. The anchor mechanism 910 may include one or more barbs 912 which extend from the sleeve body 902 and are able to flex against the outside surface of the sleeve wall 908. As shown in FIG. 20, the lumen 904 may be lined with an adhesive portion 906 such that a release liner 916 can be peeled away prior to use. In these embodiments, a physician may slide the anchor sleeve 900 over a catheter (or other medical device) and may determine the position along the catheter's length that subcutaneous anchor is desired. When the anchor sleeve 900 is disposed at the desired position along the catheter, the release liner 916 is removed to expose a pressure-sensitive adhesive layer 914. Then the anchor sleeve 900 is squeezed or compressed around the catheter to cause the anchor sleeve 900 to be firmly attached for the duration of treatment. The anchor sleeve 900 and attached catheter (or other medical device) may then be contemporaneously introduced into the patient's skin. As previously described, each barb 910 may flexibly adjust during insertion into a subcutaneous region and may flexibly adjust during removal from the patient's skin. In some circumstances, such flexing action may occur from the insertion and removal force applied to the sleeve body 902 or the attached catheter (or other medical device), without the need for a separate actuation device to extend or retract the barbs 910.

Figure 21:
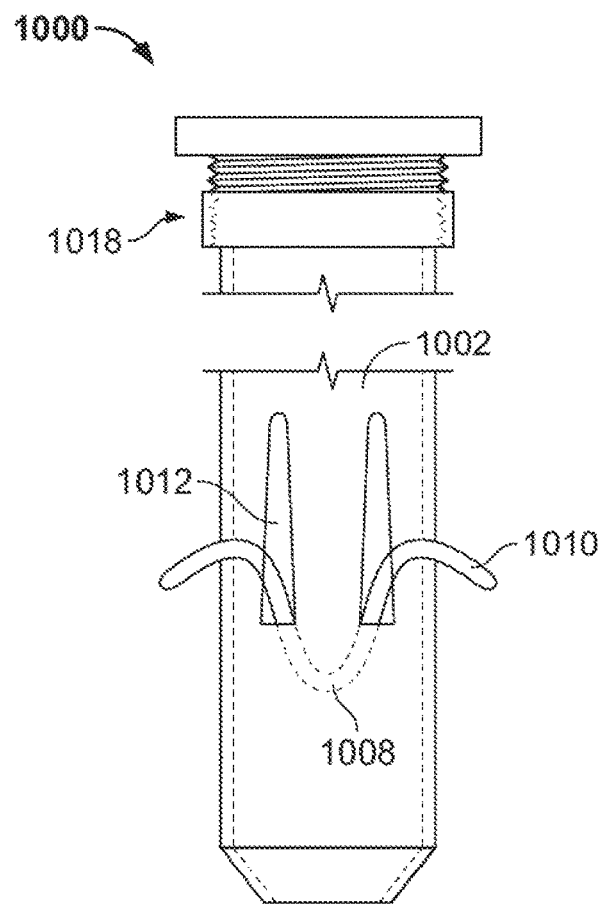
FIG. 21 is a side view of another embodiment of an anchor sleeve having an anchor mechanism secured in the anchor sleeve wall.
Figure 22:
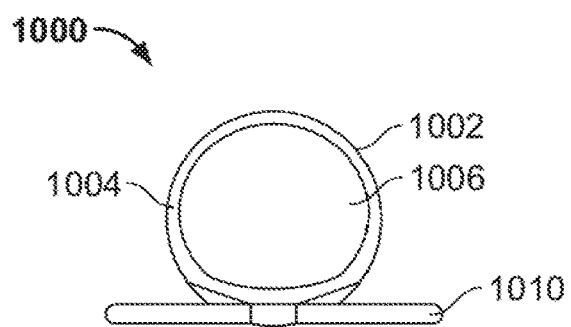
FIG. 22 is a top end view of the anchor sleeve shown in FIG. 21.

Referring now to FIGS. 21-22, some embodiments of an anchor sleeve 1000 may include an anchor mechanism 1008 that is at least partially embedded in the wall 1004 of the sleeve body 102. In this embodiment, the anchor mechanism 1008 may be integrally molded with the wall 1004, may be adhered into the wall 1004, or may be frictionally engaged within a cavity formed in the wall 1004. The anchor mechanism 1008 may comprise a nitinol material that has been processed to exhibit superelastic or shape memory characteristics, a stainless steel material, a spring steel material, titanium, MP35N and other cobalt alloys, a biocompatible polymer material, or composites thereof. For example, the anchor mechanism 1008 may be formed from a length of nitinol wire that is processed to exhibit superelastic characteristics below or at about a normal human body temperature (e.g., 37° C.). The anchor mechanism 1008 may include one or more barbs 1010 which extend from the sleeve body 1002 and are able to flex against the outside surface of the sleeve body wall 1004. As shown in FIG. 21, the outer surface of the sleeve wall 1004 may be provided with recesses 1012 which temporarily receive the barbs 1010 during introduction of the anchor sleeve 1000. Such a configuration may reduce the likelihood of traumatizing the patient's skin during insertion of the anchor sleeve through a small incision. As previously described, the barbs 1010 may flexibly adjust during insertion into a subcutaneous region and may flexibly adjust during removal from the patient's skin. In some circumstances, such flexing action may occur from the insertion and removal force applied to the sleeve body 1002 or other medical device, without the need for a separate actuation device to extend or retract the barbs 1010. Optionally, a locking-hub device 1018, such as a Touhy-Borst adapter, may be disposed at a proximal portion of the sleeve body 1002 to releasably retain a catheter or other medical instrument in a lumen 1006 the sleeve body 1002.

Figure 23:
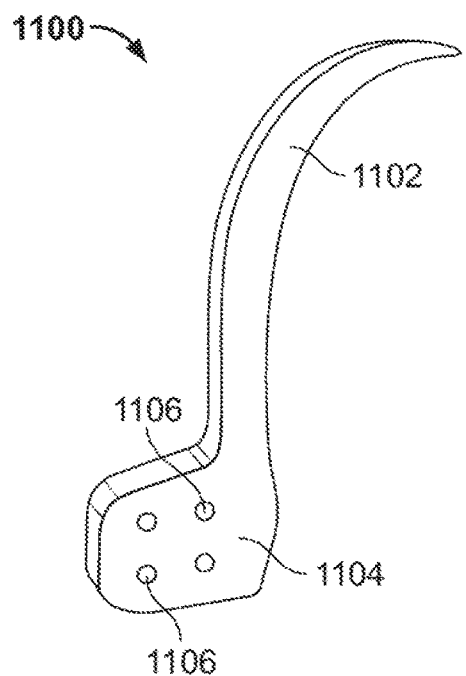
FIG. 23 is a perspective view of an embodiment of an anchor mechanism having an individual barb attachable to a catheter, anchor sleeve or other medical device.

Referring to FIG. 23, some embodiments of an anchor mechanism 1100 may be separately formed and thereafter attached to a catheter body, a sleeve body, or another medical device. The anchor mechanism 1100 may include a base 1104 which is configured to have one or more apertures 1106 extending through the base 1104. Extending from the base 1104 is at least one barb 1102, which defines a free end and a fixed end that is coupled to the base 1104. The anchor mechanism 1100 may comprise a nitinol material that has been processed to exhibit superelastic or shape memory characteristics, a stainless steel material, a spring steel material, titanium, MP35N and other cobalt alloys, a biocompatible polymer material, or composites thereof. The anchor mechanism 1100 is intended to be contained within a catheter wall (not shown) or an anchor sleeve wall (not shown) by such methods as integrally molding with the body wall, adhering into the body wall, or frictionally engaging a cavity formed in the body wall. As previously described, the barb 1102 is capable of flexing or deforming sufficiently during insertion and removal from the patient's skin so as to reduce the likelihood of trauma, and the barb 1102 may be sufficiently rigid when deployed in the subcutaneous region to secure the attached medical device (not shown) to the patient's skin for the duration of the treatment.

Figure 24:
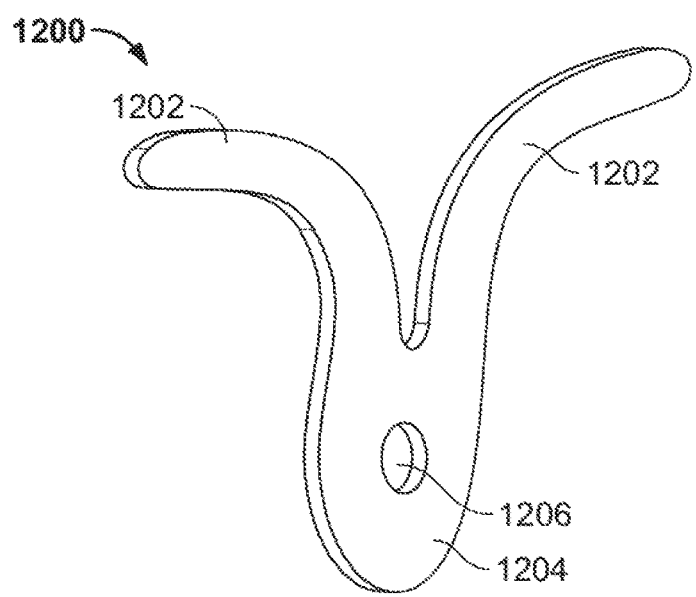
FIG. 24 is a perspective view of an alternative embodiment of an anchor mechanism having an a plurality of barbs attachable to a catheter, anchor sleeve or other medical device.

Referring to FIG. 24, other embodiments of an anchor mechanism 1200 may be separately formed and thereafter attached to a catheter body, a sleeve body, or another medical device. The anchor mechanism 1200 may include a base 1204 which is configured to have one or more apertures 1206 extending through the base 1204. One or more barbs 1202 extend from the base 1204, each of which may include a free end. The anchor mechanism 1200 may comprise a nitinol material that has been processed to exhibit superelastic or shape memory characteristics, a stainless steel material, a spring steel material, titanium, MP35N and other cobalt alloys, a biocompatible polymer material, or composites thereof. For example, the anchor mechanism 1008 may be cut from a sheet of nitinol material that is processed to exhibit superelastic characteristics below or at about a normal human body temperature (e.g., 37° C.). The anchor mechanism 1200 is intended to be contained within a catheter wall (not shown) or an anchor sleeve wall (not shown) by such methods as integrally molding with the body wall, adhering into the body wall, or frictionally engaging a cavity formed in the body wall. As previously described, each barb 1202 is capable of flexing or deforming sufficiently during insertion and removal from the patient's skin so as to reduce the likelihood of trauma, and each barb 1202 may be sufficiently rigid when deployed in the subcutaneous region to secure the attached medical device (not shown) to the patient's skin for the duration of the treatment.

A number of embodiments of the anchor mechanism or barbs have been described. It should be understood that the anchor mechanisms 22, 110, 200, 300, 404, 500, 910, 1100, 1200 or barb 604, 704, 810 could be interchanged and incorporated with an anchor sleeve, anchor catheter, or another elongated body configured to provide access through a patient's skin.

In those embodiments in which the anchor mechanism of the barb comprise a nitinol material, at least a portion of the barb may be processed to exhibit superelastic or shape memory characteristics. For example, following formation of one of the various nitinol embodiments of the anchor mechanism 22, 110, 200, 300, 404, 500, 800, 910, 1008, 1100, 1200 as described above, at least the barb 24, 112, 204, 304, 810, 912, 1010, 1102, 1202 or securing loop 410 may undergo a shape-training processed so that the barb has a desired shape upon deployment in the subcutaneous region. The shape-training process imparts superelasticity, as explained in detail below, to at least the barb 24, 112, 204, 304, 810, 912, 1010, 1102, 1202 and securing loop 410. In some embodiments, when the anchor mechanism 22, 110, 200, 300, 404, 500, 910, 1008, 1100, 1200 or barb 810 is cut or machined from its source material, it may then be placed in a forming jig that holds the barb 24, 112, 204, 304, 810, 912, 1010, 1102, 1202 or securing loop 410 in the position in which it will eventually be trained. In certain embodiments, the anchor mechanism 22, 110, 200, 300, 404, 500, 910, 1008, 1100, 1200 and barb 810 may be subjected to a temperature of 500 degrees C.+/−100 degrees C. for less than thirty minutes, depending on the alloy chemistry, dimensions, fixturing and heat source (e.g., salt bath, hot air torch, oven, or the like). A heavier and larger fixture may take a longer length of heat treatment time. Following heat treatment, the anchor mechanism 22, 110, 200, 300, 404, 500, 910, 1008, 1100, 1200 and barb 810 may be quickly cooled, for example, by an air fan.

As previously described, the anchor mechanism 22, 110, 200, 300, 404, 500, 910, 1008, 1100, 1200 or barb 810 may be formed from nitinol processed to exhibit thermal shape memory characteristics at human body temperature. Nitinol is an approximate stoichiometric alloy of nickel and titanium; however, other elements such as vanadium are sometimes added in small amounts to alter the mechanical characteristics of the alloy. Chemical composition and processing history primarily determine the particular mechanical properties of a shape memory/superelastic metallic alloy. In general, such an alloy will exist in either one or the other, or combinations of two crystallographic phases. Austenite is the parent crystallographic phase and exists at higher temperatures. Martensite is the other phase and is formed by either subjecting the alloy to lower temperatures or by placing mechanical or physical stress on the alloy while it is in the austenitic phase. Transition temperatures between these two phases can be experimentally determined for a particular alloy. Processing history includes high temperature annealing as well as low temperature forming and deformation. Following standard material and processing specifications, the transitional temperatures that define the alloy's mechanical characteristics are predictable and controllable. Standard transitional temperature designations are given as: $M_s$ for the start of the transition to the martensitic phase, $M_f$ for completion of the transition to martensite, $A_s$ for the start of the transition to the austenitic phase, and $A_f$ for the completed transition to austenite.

It is believed that superelasticity is based on phase transition from austenite to martensite. Mechanically induced phase transition from austenite to martensite occurs when the alloy temperature is above $A_f$ and a physical restraint is applied to the alloy. As long as the restraint is in place, the portion of the alloy receiving the stress reverts to the martensitic phase, which remains as long as the stress is maintained. Unless the shape recovery limits are exceeded, when the restraint is removed and the stress is released the alloy returns to its original austenitic phase and shape as long as the temperature is maintained above $A_f$. Thus, when the austenitic, trained shape of the alloy is deformed and held by stress in a new shape, a certain amount of force is exerted by the alloy against the restraint as it resists the new, untrained shape.

These alloys may also exhibit a thermal shape memory effect. Thermal shape memory occurs as the result of a piece of shape memory alloy metal being deformed while in the lower temperature martensitic phase and then being reheated to a temperature somewhere above $A_s$ which causes the alloy to reform in the austenitic phase. When the crystallographic nature of the alloy is completely austenitic, the alloy's shape returns to the previously trained shape. Shape memory training occurs when a thermal shape memory/superelastic metallic alloy is annealed (or heat-treated) while restrained in a certain shape. The trained shape will then be maintained unless it is deformed while in the low temperature martensitic phase. Upon reheating the alloy to the austenitic phase, the original shape, which was "learned" in the annealing process, will be "remembered" and returned to. Thus, temperature change is one way of controlling the crystallographic phase of a shape memory/superelastic metallic alloy.

One practical benefit of a shape memory/superelastic alloy over non-superelastic materials is that it can be deformed to a far greater degree without taking a permanent set or kink. In the case of superelastic alloys (e.g., alloys processed to exhibit superelasticity at body temperature), assuming the alloy is above the $A_f$ temperature, removal of the restraint alone may be sufficient to resume the original, trained shape. When the alloy is processed to have shape memory characteristics, the martensitic phase alloy need only be subjected to temperatures somewhere above $A_f$ and the alloy will eventually return to its original, trained shape. It is also possible to use a restraint in conjunction with alloys trained to exhibit thermal shape memory characteristics.

Accordingly, when some embodiments of an anchor mechanism 22, 110, 200, 300, 404, 500, 910, 1008, 1100, 1200 or barb 810 made of nitinol are processed to exhibit superelastic characteristics below or at about a normal human body temperature, it may employ superelasticity in two different ways. First, superelasticity (stress-induced martensite) allows the anchor mechanism 22, 110, 200, 300, 404, 500, 910, 1008, 1100, 1200 or barb 810 to be repeatedly deformed without taking a permanent set or kink. Secondly, the barb 24, 112, 204, 304, 810, 912, 1010, 1102, 1202 or securing loop 410 can be processed as described above to "program" an estimated maximum amount of force that can be applied before the barb 24, 112, 204, 304, 810, 912, 1010, 1102, 1202 and securing loop 410 will begin to flex. The advantage to this property is that when an amount of force that has been predetermined to cause little or no tissue damage to the patient's skin or subcutaneous layer, the barb 24, 112, 204, 304, 810, 912, 1010, 1102, 1202 or securing loop 410 may be "programmed" to flex at this threshold level of force. As such, the barb 24, 112, 204, 304, 810, 912, 1010, 1102, 1202 or securing loop 410 will temporarily flex (as shown, for example, in FIGS. 4-6, 7-9, and 12-13), allowing the physician to readily introduce or remove the device 10, 100, 200, 300, 400, 500, 800, 900, 1000 (and any attached medical device) with a reduced likelihood of traumatizing to the patient's.

A number of embodiments of the invention have been described. Nevertheless, it will be understood that various modifications may be made without departing from the spirit and scope of the invention. Accordingly, other embodiments are within the scope of the following claims.

What is claimed is:

1. A system for anchoring a medical device to skin of a patient, comprising:
    a tubular catheter configured to advance through a skin penetration point, the tubular catheter comprising a proximal end portion configured to reside external to the skin penetration point, a longitudinal axis, an inner lumen, and an outer tubular wall extending for a longitudinal length from the proximal end portion to a distal tip; and
    a plurality of subcutaneous anchors fixed to and extending outwardly from the outer tubular wall of the tubular catheter at a position that is located proximally from the distal tip of the tubular catheter and that is located distally of the proximal end portion of the tubular catheter, the plurality of anchors being non-retractable and positioned outwardly from the outer tubular wall of the tubular catheter during insertion of the plurality of subcutaneous anchors through the skin penetration point, each of the plurality of anchors including a free end;
    wherein the anchors are positionable between an insertion orientation when the tubular catheter is inserted into a subcutaneous layer and a removal orientation when the tubular catheter is withdrawn from the subcutaneous layer that is different from an insertion orientation, and wherein in the insertion orientation the plurality of subcutaneous anchors are positioned outwardly from the outer tubular wall of the tubular catheter and the free ends of the anchors extend towards a proximal direction, and in the removal orientation the plurality of subcutaneous anchors are positioned outwardly from the outer tubular wall of the tubular catheter and the free ends of the anchors extend towards a distal direction.

2. The system of claim 1, wherein the plurality of subcutaneous anchors are flexibly adjustable between the insertion orientation and the removal orientation.

3. The system of claim 2, wherein the plurality of subcutaneous anchors comprise a bio-compatible polymer material that is configured to elastically flex during insertion of the plurality of subcutaneous anchors through the skin penetration point and configured to elastically flex or plastically deform during withdrawal of the plurality of subcutaneous anchors through the skin penetration point.

4. The system of claim 1, wherein the plurality of subcutaneous anchors are permanently coupled to the outer tubular wall of the tubular catheter at the position that is located proximally from the distal tip of the tubular catheter and that is located distally of the proximal end portion of the tubular catheter.

5. The system of claim 1, wherein the plurality of subcutaneous anchors comprise at least two anchor barbs that extend outwardly away from one another, the free end of each of the anchor barbs being biased to extend outwardly away from the outer wall of the tubular catheter.

6. The system of claim 1, wherein the plurality of subcutaneous anchors are self-actuated to deploy in the subcutaneous layer without the need for a separate actuation device to extend or retract the subcutaneous anchors.

7. The system of claim 6, wherein the subcutaneous anchors are configured to be inserted through the skin penetration point by a pushing force to the proximal end portion of the tubular catheter such that the plurality of subcutaneous anchors advance through the skin penetration point.

8. The system of claim 7, wherein the subcutaneous anchors are configured to be withdrawn through the skin penetration point by a pulling force to the proximal end portion of the tubular catheter such that the plurality of subcutaneous anchors are removed through the skin penetration point.

9. The system of claim 1, wherein the plurality of subcutaneous anchors comprise at least two subcutaneous anchors that are fixed to and extend outwardly from the outer tubular wall of the tubular catheter such that the two subcutaneous anchors are spaced a same longitudinal distance from the distal tip of the tubular catheter.

10. A system for anchoring a medical device to skin of a patient, comprising:
    a tubular catheter configured to advance through a skin penetration point, the tubular catheter comprising a proximal end portion configured to reside external to the skin penetration point, a longitudinal axis, an inner lumen, and an outer tubular wall extending for a longitudinal length from the proximal end portion to a distal tip; and
    a plurality of subcutaneous anchors fixed to and extending outwardly from the outer tubular wall of the tubular catheter at a position that is located proximally from the distal tip of the tubular catheter and that is located distally of the proximal end portion of the tubular catheter, the plurality of anchors being non-retractable and positioned outwardly from the outer tubular wall of the tubular catheter during insertion of the plurality of subcutaneous anchors through the skin penetration point;
    wherein the anchors are positionable between an insertion orientation when the tubular catheter is inserted into a subcutaneous layer and a removal orientation when the tubular catheter is withdrawn from the subcutaneous layer that is different from an insertion orientation, and wherein in the insertion orientation and in the removal orientation the plurality of subcutaneous anchors are positioned outwardly from the outer tubular wall of the tubular catheter;
    wherein each of the subcutaneous anchors extend outwardly in a convexly curved shape when the subcutaneous anchors are deployed in the subcutaneous layer along an underside of the skin layer; and
    wherein each of the plurality of anchors include a free end, and wherein in the insertion orientation the free ends of the anchors extend towards a proximal direction, and in the removal orientation the free ends of the anchors extend towards a distal direction.

11. The system of claim 10, wherein the plurality of subcutaneous anchors comprise at least two anchor barbs that extend outwardly away from one another, the free end of each of the anchor barbs being biased to extend outwardly away from the outer wall of the tubular catheter.

12. The system of claim 11, wherein in the removal orientation the plurality of subcutaneous anchors are positioned outwardly from the outer tubular wall of the tubular catheter.

13. The system of claim 12, wherein the subcutaneous anchors are configured to be inserted through the skin penetration point by a pushing force to the proximal end portion of the tubular catheter such that the plurality of subcutaneous anchors advance through the skin penetration point.

14. The system of claim 13, wherein the subcutaneous anchors are configured to be withdrawn through the skin penetration point by a pulling force to the proximal end portion of the tubular catheter such that the plurality of subcutaneous anchors are removed through the skin penetration point.

15. The system of claim 14, wherein the plurality of subcutaneous anchors are configured to provide a holding force of about 2 lbs. to about 3 lbs. when the plurality of subcutaneous anchors secure the tubular catheter in the subcutaneous layer.

16. A system for anchoring a medical device to skin of a patient, comprising:
- a tubular catheter configured to advance through a skin penetration point, the tubular catheter comprising a proximal end portion configured to reside external to the skin penetration point, a longitudinal axis, an inner lumen, and an outer tubular wall extending for a longitudinal length from the proximal end portion to a distal tip; and
- a plurality of subcutaneous anchors fixed to and extending outwardly from the outer tubular wall of the tubular catheter at a position that is located proximally from the distal tip of the tubular catheter and that is located distally of the proximal end portion of the tubular catheter, the plurality of anchors being non-retractable and positioned outwardly from the outer tubular wall of the tubular catheter during insertion of the plurality of subcutaneous anchors through the skin penetration point;
- wherein the anchors are positionable between an insertion orientation when the tubular catheter is inserted into a subcutaneous layer and a removal orientation when the tubular catheter is withdrawn from the subcutaneous layer that is different from an insertion orientation, and wherein in the insertion orientation and in the removal orientation the plurality of subcutaneous anchors are positioned outwardly from the outer tubular wall of the tubular catheter;
- wherein the plurality of subcutaneous anchors are configured to provide a holding force of about 2 lbs. to about 3 lbs. when the plurality of subcutaneous anchors secure the tubular catheter in the subcutaneous layer; and
- wherein each of the plurality of anchors include a free end, and wherein in the insertion orientation the free ends of the anchors extend towards a proximal direction, and in the removal orientation the free ends of the anchors extend towards a distal direction.

* * * * *